(12) United States Patent
Pakzaban

(10) Patent No.: US 7,677,801 B2
(45) Date of Patent: Mar. 16, 2010

(54) NON-INVASIVE METHOD AND APPARATUS TO LOCATE INCISION SITE FOR SPINAL SURGERY

(76) Inventor: Peyman Pakzaban, 5388 Lynbrook Dr., Houston, TX (US) 77056

( * ) Notice: Subject to any disclaimer, the term of this patent is extended or adjusted under 35 U.S.C. 154(b) by 137 days.

(21) Appl. No.: 12/143,683

(22) Filed: Jun. 20, 2008

(65) Prior Publication Data
US 2009/0304143 A1 Dec. 10, 2009

Related U.S. Application Data

(60) Provisional application No. 61/059,807, filed on Jun. 9, 2008.

(51) Int. Cl.
*A61B 6/08* (2006.01)
(52) U.S. Cl. .................. 378/206; 378/162; 378/205
(58) Field of Classification Search ............... 378/205, 378/206, 162, 163, 164
See application file for complete search history.

(56) References Cited

U.S. PATENT DOCUMENTS

| | | | |
|---|---|---|---|
| 4,255,657 A * | 3/1981 | Lescrenier | 378/206 |
| 4,349,917 A * | 9/1982 | Moore | 378/164 |
| 4,832,049 A | 5/1989 | Matsushita et al. | |
| 5,537,453 A * | 7/1996 | Williams et al. | 378/206 |
| 5,706,324 A * | 1/1998 | Wiesent et al. | 378/163 |
| 6,079,876 A * | 6/2000 | Schuetz | 378/205 |
| 6,519,319 B1 * | 2/2003 | Marino et al. | 378/163 |
| 7,241,045 B2 | 7/2007 | Skalli | |
| 2006/0029186 A1 * | 2/2006 | De Villiers et al. | 378/163 |

OTHER PUBLICATIONS

Pakzaban, Peyman, "A noninvasive laser-guided preincision localizer for spine surgery", Journal of Neurosurgery: Spine, vol. 10, No. 2, (Feb. 2009), pp. 145-153.*

* cited by examiner

*Primary Examiner*—Chih-Cheng G Kao
(74) *Attorney, Agent, or Firm*—Louis Ventre, Jr.

(57) ABSTRACT

A non-invasive means and method locates a target spinal segment on a patient prior to surgery. An apparatus comprises a frame; a plurality of laser diodes projecting planar beams and mounted on the perimeter of the frame; a radio-opaque cable attached to the frame at the location of a laser diode; optionally, a weight is attached to the cable; optionally a rod extends from the frame perimeter; and optionally a bombsight is included within the frame marked with crosshairs. The method comprises the steps of marking a patient's skin; placing the frame on the patient; turning on the laser diodes; rotating the frame until the until a line of visible light is perpendicular to the patient's spine; aligning the cable with the planar laser beam; providing an X-ray source; aligning the X-ray source with the planar laser beam and obtaining an X-ray.

12 Claims, 5 Drawing Sheets

NON-INVASIVE METHOD AND APPARATUS TO LOCATE INCISION SITE FOR SPINAL SURGERY

TECHNICAL FIELD

In the field of surgery, a device and method diagnostically locates the incision site for an abnormality in the spine incident to surgery.

BACKGROUND ART

Before making a skin incision for spine surgery, it is necessary to locate the vertebral segment that contains the pathology and which is the target of the operation. Currently, this task is performed by needle localization.

In needle localization, the surgeon estimates the location of the skin incision based on palpation of anatomical landmarks, inserts a needle into the skin and advances it toward the spine. An X-ray is obtained. The surgeon then compares the location of the needle on the X-ray image to the known level of pathology based on pre-operative imaging studies (e.g. MRI or CT scan) and determines if his estimate was correct. If not, the needle is repositioned and the X-ray procedure is repeated until the correct spinal segment is located.

While not incident to surgery and not relevant to finding the incision site using X-rays, the use of laser beams to aid in detecting spinal abnormalities is known. For example, U.S. Pat. No. 4,832,049 discloses an apparatus for detecting an abnormality of the spinal column using at least one laser light beam obliquely applied to each of the left and right backs of a subject in parallel with an imaginary spinal line. The '049 patent permits detection of the imbalance of protuberances of the left and right backs based on the curvature of the spinal column. The prior art represented by the '049 patent is in general diagnostic evaluation for determining the existence of a spinal abnormality, but is generally not sufficiently specific as to the surgical incision point, that is for localizing the site in preparation for surgery.

The use of radio-opaque markers with X-rays is also known. For example U.S. Pat. No. 7,241,045 discloses radio-opaque markers attached to a frame in a stereoradiographic device having an X-ray source and a vertical X-ray receiver. The present invention uses at least one radio-opaque cable but in a device and configuration that is not disclosed in the prior art.

SUMMARY OF INVENTION

An improved means and method is disclosed for non-invasively locating a target spinal segment on a patient prior to surgery. Preferably, the apparatus comprises a frame having a solid material perimeter that defines a central area, a top and a bottom.

The apparatus comprises at least two, and preferably four, laser diodes each operable to project a planar laser beam which is projected as a line of visible light on the surfaces it encounters. The laser diodes are mounted on the perimeter of the frame.

When two laser diodes are employed they are mounted opposite each other as is shown in FIG. 5. In this case, an elongated member (512) or rod optionally extends from the perimeter of the ring at 90 degrees from the two axial laser diodes (110). When four laser diodes are employed, they are mounted at right angles to each other as is shown in FIG. 2.

The apparatus comprises a cable made of a radio-opaque material, and preferably two cables, wherein each cable is attached to the frame at the location of two diametrically opposed laser diodes.

Optionally, the apparatus comprises a weight attached to each of the cables.

Optionally, the apparatus comprises a bombsight within the central area of the frame made of a transparent material marked with crosshairs aligned with a planar laser beam and preferably with four beams of light.

Preferably, the method of the invention comprises a step of marking a patient's skin where the targeted spinal segment is estimated to be located.

The method comprises a step of placing the frame on the patient lying in a prone position.

When the bombsight is present, the method comprises a step of placing the frame such that the crosshairs are over the marking.

The method comprises a step of turning on the laser diodes.

The method comprises a step of rotating the frame until a line of visible light is perpendicular to the patient's spine. This occurs when a horizontal line connecting the two laser diodes that are positioned at 180 degrees apart from each other is perpendicular to the patient's spine.

When the rod is present, the method comprises aligning the rod with the patient's spine.

The method comprises a step of aligning the cable with a planar laser beam.

The method comprises steps of providing and X-ray source and adjusting the X-ray source side-to-side until a planar laser beam approximately centers on the X-ray source.

The method comprises a step of obtaining an X-ray wherein X-ray film is positioned for a lateral view of the spine and frame.

TECHNICAL PROBLEM

The needle localization method found in the prior art is invasive and has considerable disadvantages, including: Insertion of a needle before the skin is sterilized increases the risk of infection of the surgical site; insertion of a needle after the skin is sterilized results in a delay in making the incision, since the surgeon has to wait for the X-ray to be processed; unsterile X-ray equipment has to come close to the sterile operative field, increasing the risk of contamination; contamination risk increases if the needle localization procedure has to be repeated; insertion of the needle tends to traumatize the underlying tissues and blood vessels; the inserted needle is sometimes poorly visible on an X-ray in obese patients and with sub-optimal X-ray technique; the use of a larger needle to compensate for poor visibility further traumatizes the tissues; if the needle is inserted too deeply, the dura may be punctured; if the needle is inserted too superficially or at an angle to the spine, inaccurate localization may result.

ADVANTAGEOUS EFFECTS OF INVENTION

The invention has advantages over the standard needle localization technique because it allows for rapid, accurate, and non-invasive localization of the correct spinal segment before the skin is sterilized. The preferred embodiment uses line-emitting laser sources to project alignment lines on the skin surface and the X-ray equipment. The laser lines are used to align the target site with the X-ray source, the X-ray film (or digital capture device), and, preferably, two weighted radio-opaque cables hanging on either side of the patient. The resulting X-ray image contains the image of the superimposed cables traversing the targeted spinal segment.

BRIEF DESCRIPTION OF DRAWINGS

The reference numbers in the drawings are used consistently throughout. New reference numbers in FIG. 2 are given the 200 series numbers. Similarly, new reference numbers in each succeeding drawing are given a corresponding series number beginning with the figure number.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural and operational changes may be made without departing from the scope of the present invention.

Figure 1:
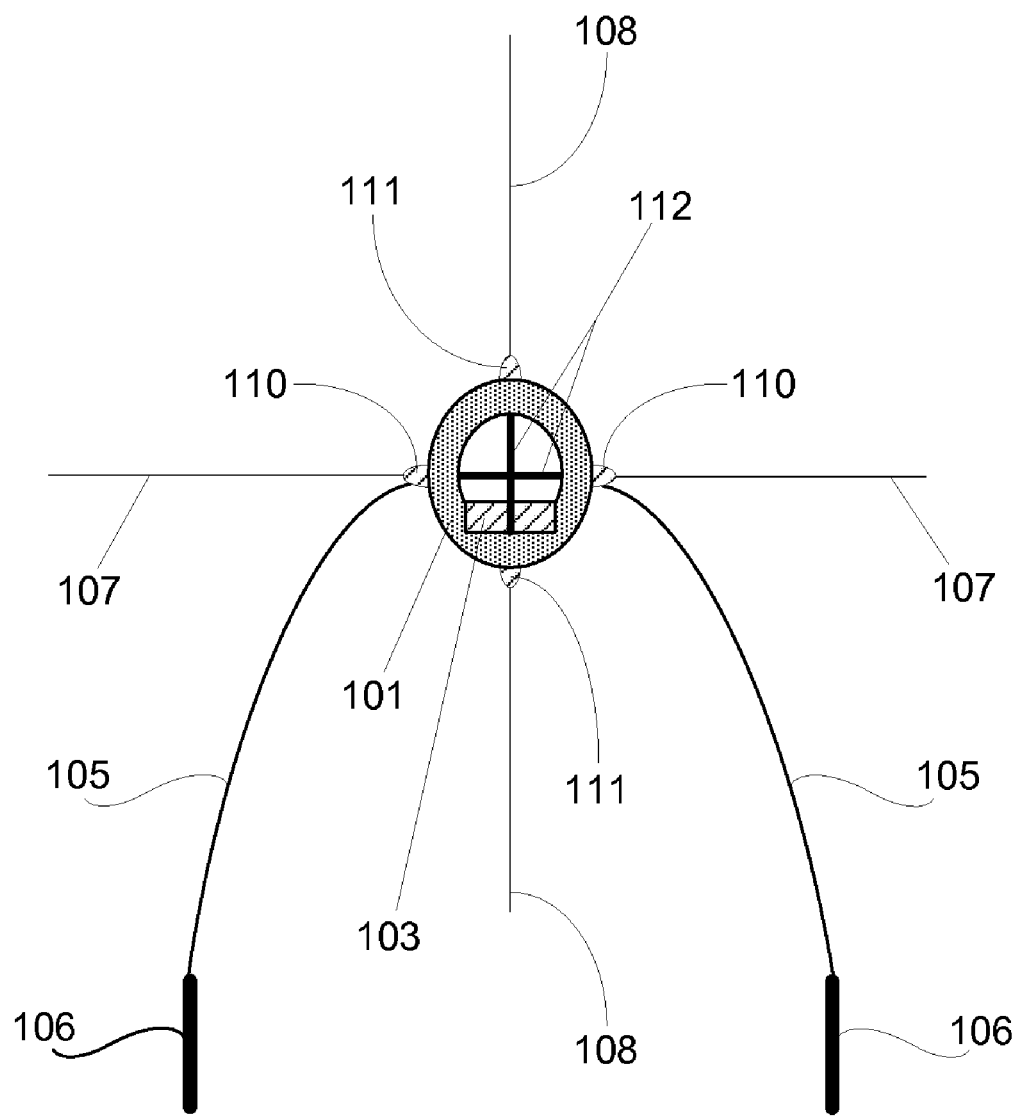
FIG. 1 is a top view of a preferred embodiment of the apparatus.
Figure 5:
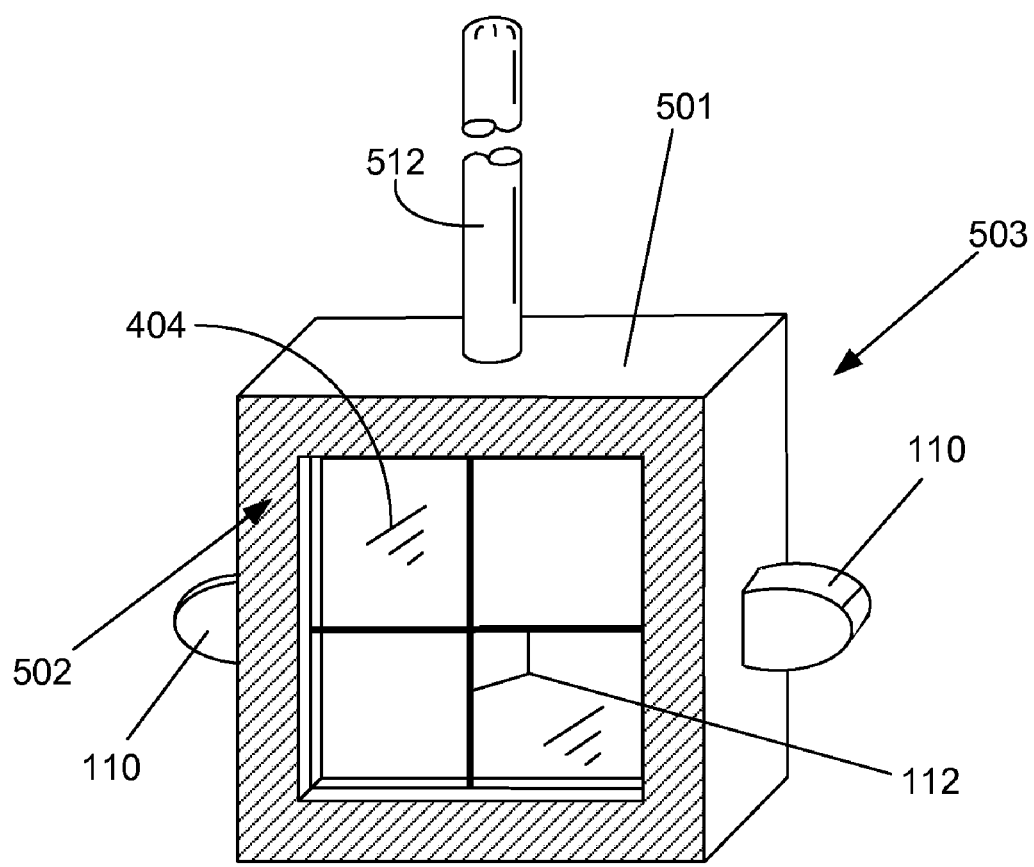
FIG. 5 is a perspective of a preferred frame showing its top and bottom surrounding a bombsight with crosshairs and mounted laser diodes.

FIG. 1 shows top view of a preferred embodiment of an apparatus to locate a target spinal segment prior to surgery on a patient. A first component of the apparatus is a frame (101). A round or ring frame is shown in FIG. 1. However, the frame (101) may have any geometrical shape. For example, a square frame (501) is shown in FIG. 5. The frame (101), similar to a picture frame, has a solid material perimeter defining a central area, a top (502) and a bottom (503). The central area may be vacant.

A second component of this apparatus is plurality of laser diodes (110 and 111), and preferably four laser diodes. Each laser diode is mounted on the perimeter of the frame (101). Each laser diode is operable to project a planar laser beam outwardly from the center of the frame (101).

While identical in physical form, two of the laser diodes are defined as axial laser diodes (110) because they project a planar laser beam to the sides of a patient, and two are defined as sagittal laser diodes (111) because they project a planar laser beam along a patient's spine. The planar laser beam projected from both an axial laser diode and the sagittal laser diode creates a line of visible light on the surfaces it encounters.

Application of the term "axial" herein is consistent with its use in medicine and radiology. The axial plane is perpendicular to the sagittal plane and divides the body into top and bottom portions. The cross section of the patient's torso (213) in FIG. 3 is in the axial plane as are the two axial planar laser beams (107).

A minimal embodiment of the invention has two axial laser diodes (110) positioned at 180 degrees apart from each other, and thus produces two axial planar laser beams (107) one on the X-ray source (209) and one on the image capture device (210). The image capture device (210) is the X-ray film, digital capture device or other such image receiver Alternatively, mirrors and prisms might be employed to allow one laser diode to project two or more lines—potentially, four lines formed perpendicularly to each other.

However, preferably, as shown in FIG. 1, there are four such laser diodes mounted on the frame at right angles to each other. Two are termed sagittal laser diodes (111), which produce two sagittal planar laser beams (108) forming a line of light along the spinal column. The other two are termed axial laser diodes (110) and produce two axial planar laser beams (107) projected to the sides of a patient.

Figure 3:
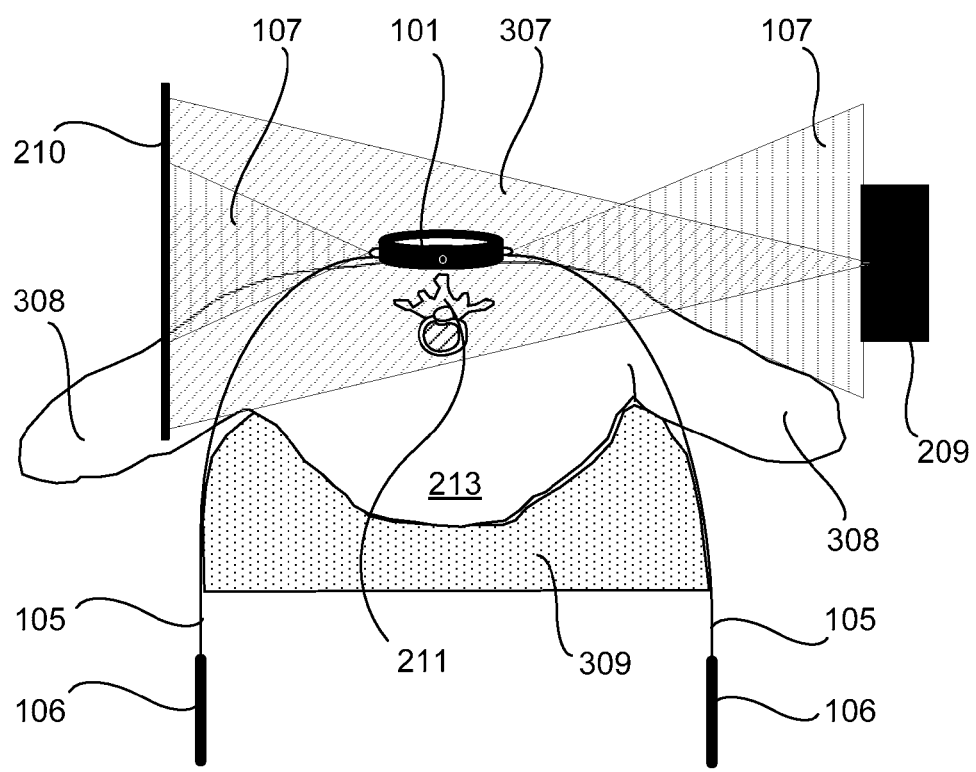
FIG. 3 is an elevation view of a preferred embodiment of the apparatus viewed over a cross-section of a patient's torso where the patient is lying in a prone position.

The axial laser diodes (110) for the axial planar laser beams (107) are properly aligned when an imaginary horizontal line connecting these two axial laser diodes (110) is perpendicular to the patient's spine when the bottom of the frame is positioned on the patient's spine (211) for a patient lying horizontally and facing down, that is in a prone position, as shown in FIG. 3. These two axial planar laser beams (107) are used to align the X-ray source (209), the image capture device (210), and one or two cables, both designated (105), depending on the embodiment.

Such laser diodes are well known in the art and can either produce: a linear beam projecting a point at a distance, such as a laser pointer; or, planar laser beam that projects a line of visible light on the surfaces it encounters. The kind considered the best for this application is a planar laser beam.

A planar laser beam is easier to use than a linear beam because it forms a visible line of light on the object: the two sagittal planar laser beams (108) form two lines on the patient's body over the spine, and the two axial planar laser beams (107) form two vertical lines of visible light: one on the X-ray source and one on the image capture device (210).

FIG. 3 illustrates an elevation view of the illumination field of two axial planar laser beams (107) in a preferred embodiment and the illumination cross-section of X-rays beam (307) recorded on the image capture device (210). The patient is lying in a prone position with arms (308) to the left and right of an operating table (309).

Figure 4:
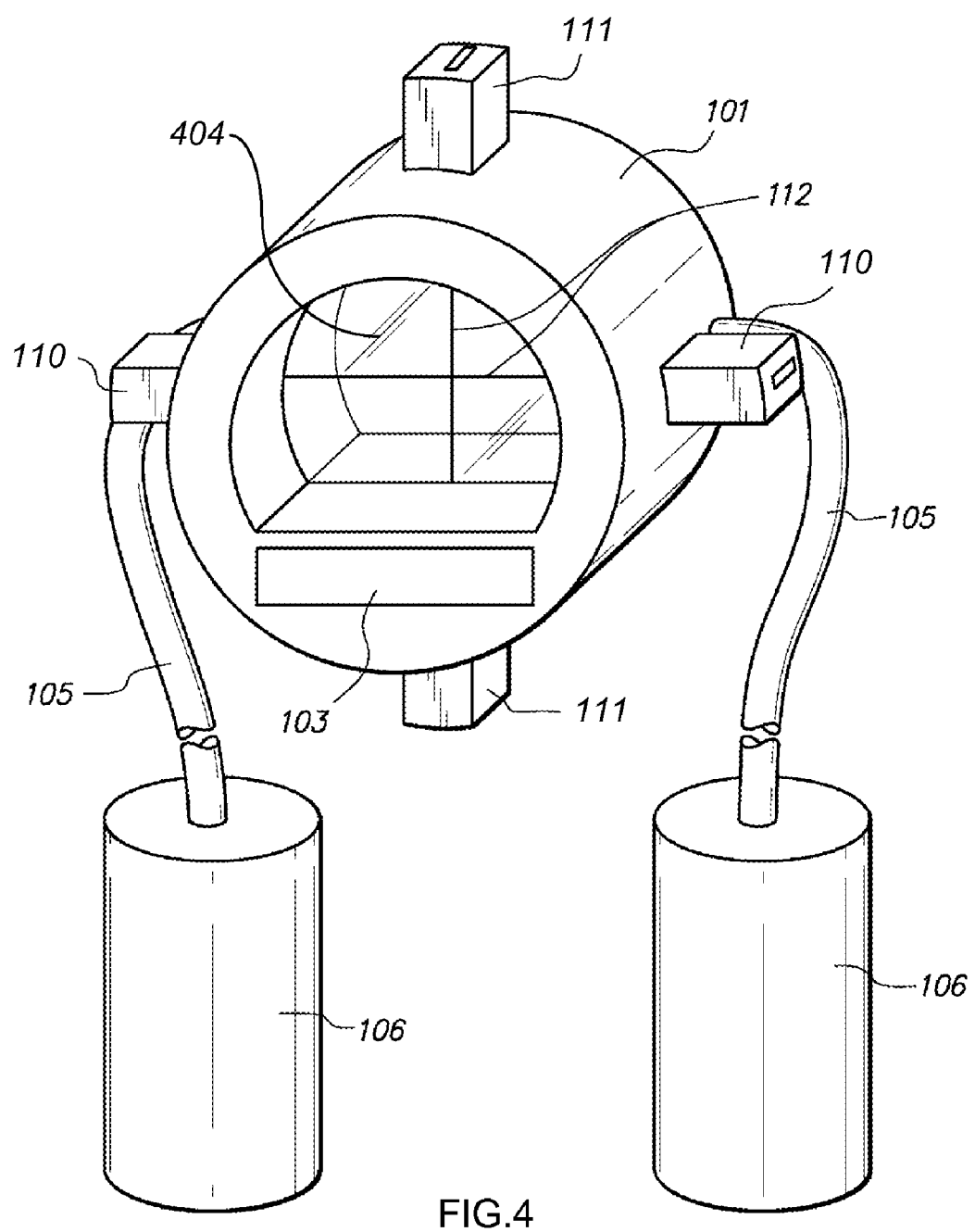
FIG. 4 is a perspective of a preferred embodiment of the apparatus.

FIG. 4 illustrates an embodiment of an optional component of this apparatus, namely, a bombsight (404) within the central area of the frame (101). FIG. 5 also shows the bombsight (404) with the central area of a square frame (401). The bombsight (404) comprises a transparent material marked with crosshairs (112). One crosshair is aligned with the two axial laser diodes (110). Preferably when four laser beams are produced, the crosshairs are aligned with the four laser beams. It is termed a bombsight because in use, a person aligns the crosshairs while looking through the bombsight (404) over markings on the patient's skin estimated as the incision site.

A fourth component of this apparatus is a cable (105) made of a radio-opaque material wherein the cable (105) is attached to the frame (101) at the location of a laser diode (110). A minimal embodiment uses only a single flexible cable (105), but there are preferably two cables on each side of the frame (101). If one cable is used, the cable is preferably positioned on the side of the patient closest to the image capture device (210). When two cables (105) are used, they are mounted at diametrically opposed axial laser diodes (110). The cable (105) may be retractable. Use of the term cable herein is broadly defined to include retractable radio-opaque tape or a foldable articulated radio-opaque arm, or such other radio-opaque device that produces a well defined line in an X-ray.

Figure 2:
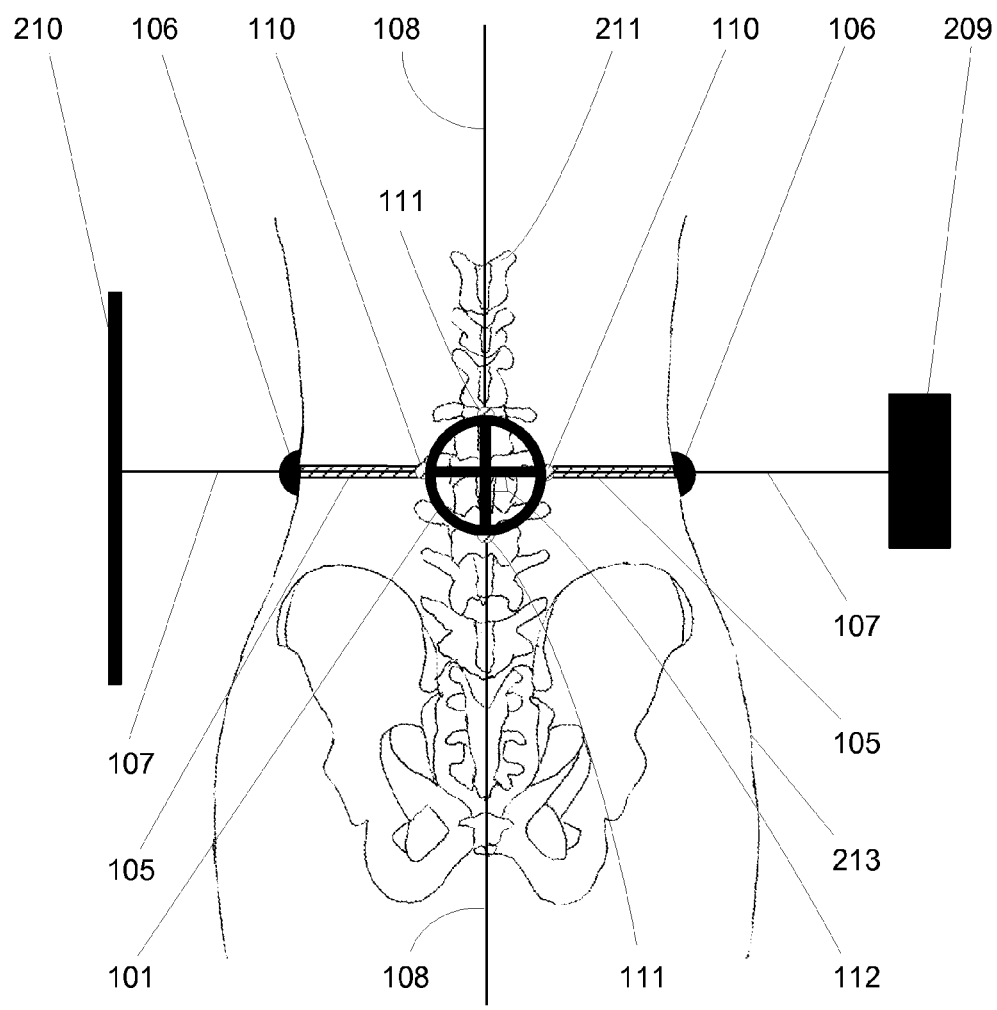
FIG. 2 is a top view of a preferred embodiment of the apparatus positioned on a patient's back where the patient is lying in a prone position.

As shown in FIG. 2, a cable (105) in use, hangs down to each side of the patient's torso (213). The function of the cable (105) is to create a line on the X-ray at the image capture device (210) that helps to identify the orientation of the image and the exact vertebral segment marked for surgery. When two cables are used, two lines on the X-ray help to identify any lateral offset of the X-ray source (209).

When the cable comprises a material or design that does not hang straight, an optional fifth component of the apparatus is a weight (106) attached to the cable (105). The weight (106) helps to stretch the cable (105) taut by action of gravity. There is an optional weight (106) for each cable (105) used in an embodiment. Thus, when two cables (105) are used in a preferred embodiment as shown in FIG. 3, there a weight (106) may be attached to each cable (105). Each weight (106) ideally hangs above the floor at the sides of the operating table (309).

The laser diodes may be made operable by battery power or by direct connection to an electrical outlet. Use of batteries is preferably enabled by a battery compartment (103) which also houses the electronic circuitry necessary for operability of the laser diodes. The battery compartment may be attached to the frame (101) or remotely connected to the laser diodes (110 and 111) by wires.

In the preferred method of using the apparatus, there are multiple steps which may be performed in any order that results in finding the optimal incision point for surgery on a patient's spine.

A first step is marking a patient's skin where the spinal segment is estimated to be located.

A second step is placing the frame (101) on the patient lying in a prone position such that the crosshairs (112) are over the marking.

A third step is turning on the laser diode.

A fourth step is rotating the frame (101) until a beam of visible light aligns perpendicularly to the patient's spine (211), which is approximated to the patient's body midline. If the embodiment has four laser diodes, then one diametrically opposed pair will create two sagittal planar laser beams (108) aligned with the patient's spine (211) and the other pair will necessarily produce two axial planar laser beams (107) aligned perpendicularly to the patient's spine (211). This latter pair is also the pair at which the cables are attached in a preferred embodiment having two cables. When two cables (105) are present, one is placed between the patient and the X-ray source (209) and the other is placed between the patient and the image capture device (210) on either side of the patient.

A fifth step is aligning the cable (105) with a planar laser beam projected to a side of the patient.

A sixth step is obtaining an X-ray positioned for a lateral view of the patient's spine (211) and frame (101). The X-ray source (209) is positioned in the usual fashion to obtain a lateral X-ray of the patient's spine (211) and to make sure the X-ray beam (307) covers the X-ray film or digital capture area on the image capture device (210).

A seventh step is providing an X-ray source (209).

An eighth step is adjusting the X-ray source (209) side-to-side until an axial planar laser beam approximately centers on the X-ray source (209). Most portable X-ray machines have crosshairs on the X-ray source (209), in which case the vertical line created by one of the axial planar laser beams (107) traverses the intersection of the crosshairs on the X-ray source (209).

The method may include step of providing an image capture device (210); and adjusting the image capture device (210) side-to-side until one of the axial planar laser beams (107) approximately centers on the image capture device (210).

Obviously, the method of the invention permits examination of the X-ray that is taken. If satisfactory, the skin is then heavily marked with a surgical marker along the length of the cable (105), and the apparatus is removed from the patient. The surgical site is prepped and draped in sterile fashion. A skin incision is made, centered on the marked line.

Obvious alternatives to the preferred embodiments employ radio-opaque markers mounted directly on the X-ray film or digital capture device, or X-ray source. Also, the laser diodes can be mounted directly on the X-ray source and/or the X-ray film or digital capture device.

INDUSTRIAL APPLICABILITY

The invention has application to the medical industry and more specifically to physicians and diagnosticians performing or supporting spinal surgery.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

What is claimed is:

1. An apparatus to locate a target spinal segment prior to surgery on a patient comprising:
   (a) a frame comprising a solid material perimeter defining a central area, a top and a bottom;
   (b) a plurality of laser diodes mounted on the perimeter of the frame, each operable to project a planar laser beam which is projected as a line of visible light on the surfaces it encounters, wherein two laser diodes are positioned at 180 degrees apart from each other and,
   (c) a cable comprising a radio-opaque material wherein the cable is attached to the frame at the location of a laser diode.

2. The apparatus of claim 1 further comprising a weight attached to the cable.

3. The apparatus of claim 1 further comprising a bombsight within the central area of the frame comprising a transparent material marked with a crosshair aligned with the two laser diodes.

4. The apparatus of claim 1 further comprising an elongated member that extends from the perimeter of the frame at 90 degrees from the two laser diodes that are positioned at 180 degrees apart from each other.

5. The apparatus of claim 1 comprising a total of four laser diodes each operable to project a planar laser beam and mounted on the frame at right angles to each other.

6. The apparatus of claim 1 wherein the cable is sized to be tautly stretched by gravity to a side of a patient lying in a prone position on an operating table.

7. The apparatus of claim 1 comprising a total of two cables mounted at diametrically opposed laser diodes.

8. The apparatus of claim 1 further comprising a battery compartment attached to the frame.

9. A method of using the apparatus of claim 1 comprising the steps of:
   (a) marking a patient's skin where the spinal segment is estimated to be located;
   (b) placing the frame on the patient lying in a prone position;
   (c) turning on the laser diodes
   (d) rotating the frame until a line of visible light is perpendicular to the patient's spine;
   (e) aligning the cable with a planar laser beam
   (f) providing an X-ray source;

(g) adjusting the X-ray source side-to-side until a planar laser beam approximately centers on the X-ray source; and, (h) obtaining an X-ray positioned for a lateral view of the spine and frame.

10. The method of claim 9 further comprising the step of providing an image capture device; and adjusting the image capture device side-to-side until the laser beam approximately centers on the image capture device.

11. The method of claim 9 further comprising the steps of providing a bombsight within the central area of the frame comprising a transparent material marked with crosshairs aligned with the beam of visible light; and aligning the crosshairs over the marking.

12. The method of claim 9 further comprising the steps of providing an elongated member protruding from the perimeter of the frame at 90 degrees from the two laser diodes that are positioned at 180 degrees apart from each other; and, aligning the elongated member with the patient's spine.

* * * * *